United States Patent
Ohodnicki et al.

(10) Patent No.: US 8,741,657 B1
(45) Date of Patent: *Jun. 3, 2014

(54) NANOCOMPOSITE THIN FILMS FOR OPTICAL GAS SENSING (71) Applicant: U.S. Department of Energy, Washington, DC (US)

(72) Inventors: Paul R. Ohodnicki, Alison Park, PA (US); Thomas D. Brown, Finleyville, PA (US)

(73) Assignee: U.S. Department of Energy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/775,447

(22) Filed: Feb. 25, 2013

(51) Int. Cl.
G01N 21/00 (2006.01)
G01N 21/55 (2014.01)

(52) U.S. Cl.
USPC .......................................... 436/102; 436/100

(58) Field of Classification Search
CPC ....... G01N 21/00; G01N 21/17; G01N 21/62; G01N 2121/258; G01N 2121/25
USPC .................................................. 436/102, 100
See application file for complete search history.

(56) References Cited

U.S. PATENT DOCUMENTS 4,355,997 A * 10/1982 Smith et al. ...................... 436/25
5,388,515 A * 2/1995 Schneider et al. ............. 101/363
5,580,793 A * 12/1996 Wanner ......................... 436/144
5,941,068 A * 8/1999 Brown et al. .................... 60/297
7,249,564 B2 * 7/2007 Lissianski et al. ............ 110/345
7,864,322 B2 1/2011 Carpenter et al.
8,308,848 B1 * 11/2012 Alptekin et al. ................ 95/136
2003/0134426 A1 * 7/2003 Jiang et al. ..................... 436/121
2004/0112743 A1 * 6/2004 Fukatsu et al. ................ 204/424
2009/0207413 A1 * 8/2009 Carpenter et al. ............ 356/437
2010/0210029 A1 * 8/2010 Meinhart et al. .............. 436/168
2011/0038784 A1 * 2/2011 Plata et al. ................. 423/447.1
2011/0152070 A1 * 6/2011 Fansler et al. ................. 502/183

OTHER PUBLICATIONS

Giangregorio et al., "Insight into Gold Nanoparticle-Hydrogen Interaction: A Way to Tailor Nanoparticle Surface Charge and Self-Assembled Monolayer Chemisorption," J. Phys. Chem. C 115 (2011).
Bus et al., "Hydrogen Chemisorption on Al2O3-Supported Gold Catalysts," J. Phys. Chem. B 109 (2005).

(Continued)

Primary Examiner — Christine T Mui
(74) Attorney, Agent, or Firm — James B. Potts; Brian J. Lally; John T. Lucas (57) ABSTRACT The disclosure relates to a plasmon resonance-based method for gas sensing in a gas stream utilizing a gas sensing material. In an embodiment the gas stream has a temperature greater than about 500° C. The gas sensing material is comprised of gold nanoparticles having an average nanoparticle diameter of less than about 100 nanometers dispersed in an inert matrix having a bandgap greater than or equal to 5 eV, and an oxygen ion conductivity less than approximately $10^{-7}$ S/cm at a temperature of 700° C. Exemplary inert matrix materials include $SiO_2$, $Al_2O_3$, and $Si_3N_4$ as well as modifications to modify the effective refractive indices through combinations and/or doping of such materials. Changes in the chemical composition of the gas stream are detected by changes in the plasmon resonance peak. The method disclosed offers significant advantage over active and reducible matrix materials typically utilized, such as yttria-stabilized zirconia (YSZ) or $TiO_2$.

20 Claims, 8 Drawing Sheets (56) References Cited

OTHER PUBLICATIONS

Joy et al., "Plasmonic Based Kinetic Analysis of Hydrogen Reactions within Au-YSZ Nanocomposites," J. Phys. Chem. C 115 (2011).
Bingham et al., "Gas Sensing with High-Resolution Localized Surface Plasmon Resonance Spectroscopy," J. Am. Chem. Soc. 132 (2010).
Nengsih et al., "Detection of Volatile Organic Compound Gas Using Localized Surface Plasmon Resonance of Gold Nanoparticles," Sains Malaysiana 40(3)(2011).

* cited by examiner

NANOCOMPOSITE THIN FILMS FOR OPTICAL GAS SENSING

GOVERNMENT INTERESTS

The United States Government has rights in this invention pursuant to the employer-employee relationship of the Government to the inventors as U.S. Department of Energy employees and site-support contractors at the National Energy Technology Laboratory.

RELATION TO OTHER APPLICATIONS

This patent application is a continuation of and claims priority from U.S. Pat. No. 8,411,275 filed Apr. 10, 2012, which is hereby incorporated by reference.

FIELD OF THE INVENTION

One or more embodiments relates to a method for sensing changes to the chemical composition in a gas at temperatures greater than approximately 500° C. utilizing changes to the plasmon resonance peak generated by a gas sensing material. The gas sensing material is comprised of a nanocomposite film comprised of a plurality of gold nanoparticles dispersed within, below, or above an optically transparent, wide bandgap matrix considered to be inert under the conditions in which the gas sensing is performed. In some cases, this matrix is specifically selected such that the nanocomposite film exhibits an effective refractive index that is less than that of the core material of an optical waveguide to enable effective waveguiding when employed as a gas sensitive cladding layer for evanescent wave absorption spectroscopy based sensing.

BACKGROUND

The enhancement of EM fields in the vicinity of metallic nanoparticles and metallic nanostructures can be explained by the phenomenon of localized surface plasmon resonance. The shape and magnitude of associated features measured in the transmission or reflection spectra from these metallic structures depend on the enhanced scattering and absorption of light at specific wavelengths. The details of the extinction cross-section enhancement over a finite wavelength range is affected by several different factors that include the characteristic optical constants and geometry of the nanostructures illuminated by incident light as well as the optical constant of the surrounding matrix phase.

The origin of plasmon resonances are collective oscillations of the conduction band electrons, and they result from the presence of interfaces for nanoparticles and films of a select group of materials which include the noble metals Ag, Cu, and Au. Localized surface plasmons are excited when light is incident on metallic nanoparticles which typically have dimensions smaller than the wavelength of the incident light. At certain characteristic wavelengths, one or more resonant modes are excited in the nanoparticles, leading to a significant enhancement in absorbed and scattered light and a strong increase in the electromagnetic fields in the vicinity of the particles. Localized surface plasmons can be detected as resonance peaks in the absorption and scattering spectra of the metallic nanoparticles. Nanostructures made up of noble metals, such as gold, silver, and copper, are well known to exhibit localized surface plasmon resonance (LSPR) phenomena.

The collective oscillation of the free electrons is also sensitive to changes in the size of the particle. For example, gold nanoparticles embedded in a transparent matrix phase with a real dielectric constant similar to that of $SiO_2$ ($\epsilon$~2.25) and average diameters in the range of approximately 5-10 nm, strongly absorb at visible wavelengths with a maximum absorbance near 520 nm. In this particular case, the energy required to excite the surface plasmon lies in the visible region of the spectrum. With increases in the Au particle size, a shift in the peak of the optical absorption to longer wavelengths is observed due to the excitation of higher-order resonant modes. The relative magnitude of the scattering cross-section also increases as compared to the absorption cross-section resulting in particles that strongly scatter light rather than absorb it for particle sizes approaching 100 nm. In addition to being site-dependent, the plasmon resonance band is sensitive to changes in the dielectric properties of the surrounding medium. For transparent matrix media with large dielectric constants, the energy required to collectively excite the electrons is decreased thereby shifting the peak in the extinction cross-section to lower energies and longer wavelengths.

The strong dependence of the optical extinction peak on a number of material dependent parameters provides the nanoparticles with an inherent sensing ability. For visible light, generally only changes in refractive index occurring at distance within about 200 nm of the particle surface result in changes to the optical properties of the nanoparticles. The plasmon resonance behavior of nanoparticles are particularly sensitive to adsorption directly on the particle surface and hence biological sensing based on analyte absorption by nanoparticles and subsequent modifications of the absorbance maximum is currently an area of significant effort.

The changes in the absorbance maxima generated by the localized surface plasmon resonance effect have also been utilized extensively for gas sensing applications in the low and intermediate temperature ranges. A select few researchers in the field have also applied Au incorporated films to optical gas sensing at higher temperatures. However, current technical literature suggests that the fundamental response of technically useful Au/metal oxide composite films requires the selection of a matrix phase that plays an active role in the gas sensing process. Two potential ways that such an active role can be played include (1) a change in the free carrier density of the matrix phase followed by an electronic charge transfer from the matrix to the nanoparticle and (2) a change in the effective dielectric constant of the matrix phase. Both of these effects would result in a modification to the extinction peak of Au nanoparticles associated with the localized surface plasmon resonance effect that could be detected through optical based monitoring techniques. As a result, nanoparticles are generally embedded in catalytically active, reducible, and oxygen conducting matrices such as $TiO_2$ or yttria-stabilized zirconium (YSZ) for high temperature (T>~500° C.) optical gas sensing. Current technical literature suggests that technologically useful optical responses in this temperature range associated with plasmon absorption peak shifts require the presence of oxygen in the sensing environment and reduction of the matrix phase with associated changes in the oxygen vacancy concentration. For lower temperatures, gold nanoparticles have been embedded in matrices of even more highly reducible oxides such as NiO, $WO_3$, or CuO. The sensing mechanism is again attributed to reduction of the matrix in the bulk or at the surface, and modifications to the real and imaginary parts of the refractive indices of the oxide may play a more significant impact on altering the position and shape of the SPR band. See e.g., Sirinakis et al., "Development and Characterization of Au-YSZ Surface Plasmon Resonance Based Sensing Materials: High Temperature Detection of CO," *J. Phys. Chem. B* 110 (2006); and see Ando et al., "Optical CO sensitivity of Au—CuO composite film by use of the plasmon absorption change," *Sensors and Actuators B* 96 (2003); and see U.S. Pat. No. 7,864,322 B2 to Carpenter et al. These approaches have the disadvantage of requiring the concurrent presence of $O_2$ as a gaseous constituent in order to affect charge transfer and/or limited stability of the oxide matrix.

Another class of dielectric matrix phases exists which exhibits improved temperature and chemical stability as compared to reducible oxides and which is characterized by a relatively wide bandgap and low oxygen and electronic conductivity commonly referred to in the literature as "inert". Examples of such inert materials include $SiO_2$, $Al_2O_3$, and $Si_3N_4$. In this class of matrix materials, direct interactions of the matrix with the ambient atmosphere are mitigated as compared to catalytically active, reducible, and oxygen conducting matrices such as $TiO_2$ and YSZ. It would be advantageous to provide a plasmon-based methodology for high temperature gas sensing based on a gas sensing material comprised of Au-nanoparticles embedded in such an inert matrix, where technologically useful responses are observed despite mitigation of interactions between the matrix material and the ambient gas atmosphere reported to be responsible for the measured sensing response in systems such as Au/YSZ. Direct interactions with oxygen conducting matrices such as YSZ generate a change in effective dielectric constant and/or a change in the concentration of oxygen vacancies with a measurable effect on the localized surface plasmon resonance (LSPR) extinction cross-section. The former impacts the LSPR behavior directly while the latter affects it through changes in the density of electrons (n-type oxides) or holes (p-type oxides) in the matrix phase, followed by charge transfer between the nanoparticle and the matrix. It would also be advantageous to provide a methodology that does not require the presence of $O_2$ within the sensing environment.

Preferably, such a methodology would generate useful responses due to a direct action between the nanoparticle and ambient chemical species, particularly at temperature in excess of approximately 500° C. Currently, plasmonic responses to such direct interactions have been limited to a gold nanoparticle/silicon substrate material exposed to atomic H at room temperature. See Giangregorio et al., "Insight into Gold Nanoparticle-Hydrogen Interaction: A Way To Tailor Nanoparticle Surface Charge and Self-Assembled Monolayer Chemisorption," J. Phys. Chem. C 115 (2011). Further, investigations on the adsorption of diatomic $H_2$ on gold nanoparticles has been limited to temperatures of around 250° C., significantly below the 500° C. or greater temperatures desired for certain operations including, but not limited to, power generation technologies utilizing fossil fuels including coal gasification, solid oxide fuel cells, gas turbines, and advanced combustion systems. See e.g., Bus et al., "Hydrogen Chemisorption on $Al_2O_3$-Supported Gold Catalysts," *J. Phys. Chem. B* 109 (2005). Other investigators have suggested that direct adsorption of $H_2$ on Au in the Au/YSZ system could be responsible for observations in $O_2$-free atmospheres at temperatures approaching 500° C., but technologically useful responses were not observed and it was indicated that measured responses could also be explained through donation of electrons to the matrix phase by atomic H+ followed by charge transfer between the matrix and Au nanoparticles leading to plasmon resonance shifts. See e.g. Joy et al., "Plasmonic Based Kinetic Analysis of Hydrogen Reactions within Au-YSZ Nanocomposites," *J. Phys. Chem. C* 115 (2011). It would be advantageous if a methodology were provided whereby nanoparticles dispersed on, beneath, or embedded within a matrix could be utilized for a plasmon-based detection of gas species generated through a direct interaction between the nanoparticles and the ambient gas species, and additionally advantageous if the methodology were effective in gas streams at temperatures in excess of approximately 500° C., such that they were relevant for a number of fossil fuel based energy production applications.

Disclosed here is a method for gas sensing utilizing shifts in a plasmon resonance peak position generated by a gas sensing material. In an embodiment, the gas is at a temperature greater than about 500° C. The gas sensing material is comprised of a plurality of gold nanoparticles dispersed in a wide bandgap matrix with a sufficiently low oxygen ion conductivity at the temperatures and gas atmospheres of interest that it is classified as "inert". The method disclosed offers significant advantage over materials typically utilized for plasmon-based high temperature sensing such as yttria-stabilized zirconia (YSZ) or $TiO_2$, including enhanced thermal and chemical stability and increased stability of nanoparticle diameter, among other advantages. In addition, several candidates for inert matrix materials (e.g. $SiO_2$, $Al_2O_3$, $MgF_2$ doped $SiO_2$, mixed $SiO_2/Al_2O_3$) exhibit relatively low values of refractive indices for fully densified films ranging from less than ~1.5 to greater than ~1.7. In contrast, such low values of effective refractive index cannot be obtained in fully dense films of reducible or high oxygen conducting oxides such as $TiO_2$ and YSZ. This property is advantageous as it enables integration of nanocomposite films directly with optical fiber based sensors as a gas sensitive cladding layer in an evanescent wave absorption spectroscopy based sensing configuration, while maintaining the conditions necessary for waveguiding in the low refractive index core material. Typical core materials for such applications include $SiO_2$ (refractive index ~1.5) for silica-based optical fibers and $Al_2O_3$ (refractive index ~1.7) for sapphire based optical fibers.

These and other objects, aspects, and advantages of the present disclosure will become better understood with reference to the accompanying description and claims.

SUMMARY

The disclosure provides a method for gas sensing by utilizing modifications to the plasmon resonance peak generated by a gas sensing material, where the gas sensing material is comprised of a plurality of gold nanoparticles disperse in an inert matrix. The gas sensing material is in contact with a monitored stream comprised of gaseous constituents and periodically comprised of a chemical species of interest, having a concentration which may vary over time. The gas sensing material exhibits changes to the plasmon resonance peak in response to changes to the chemical composition of the monitored stream, such as changes to the $H_2$, CO, and $O_2$ concentrations among others. In an embodiment, the monitored stream has a temperature greater than about 500° C.

The gas sensing material is comprised of gold nanoparticles having an average nanoparticle diameter of less than about 100 nanometers. The gold nanoparticles are dispersed in an inert matrix having a bandgap greater than or equal to 5 electron volts (eV), and an oxygen ion conductivity of less than approximately $10^{-7}$ S/cm at temperature of 700° C. Exemplary inert matrix materials include $SiO_2$, $Al_2O_3$, and $Si_3N_4$ as well as derivatives such as $MgF_2$ doped $SiO_2$, and mixtures of $SiO_2/Al_2O_3$. In certain embodiments, matrix materials are specifically chosen to optimize the effectiveness refractive index of the gas sensing material for use as gas sensitive cladding layers in optical waveguide based sensors.

Negligible changes in refractive index and a limited number of free carriers of the inert matrix are expected in response to any reducing species that may occur in a monitored stream, such that modifications to the LSPR features of Au nanoparticles can be dominated by interactions between the Au particle and the ambient atmosphere. Rather than playing an active role in the gas sensing mechanism, the primary role of the inert matrix is two-fold: (1) to mitigate the coarsening of gold nanoparticles under any high temperature conditions and (2) to tailor the effective refractive index of the nanocomposite thin film for optimized sensing response when integrated with an optical waveguide based sensing platform. In some cases, the matrix phase may also be selected to improve selectivity by inhibiting chemical diffusion of species other than the species of interest, thereby preventing them from reaching the surface of embedded Au nanoparticles.

The gas sensing material utilized in the method of this disclosure may be prepared using means known in the art for the production of gold nanoparticles dispersed within a supporting matrix, including sol-gel based wet chemistry techniques, impregnation techniques, implantation techniques, sputtering techniques, and others. The gas sensing material may be deposited as a single monolithic layer or through multi-layered deposition involving a single technique or a combination of several film deposition techniques. The gas sensing material and the associated method disclosed offers significant advantages over materials typically utilized for plasmon-based sensing such as yttria-stabilized zirconia (YSZ) or $TiO_2$, including enhanced thermal and chemical stability and increased stability of nanoparticle diameter, among others.

The novel process and principles of operation are further discussed in the following description.

DETAILED DESCRIPTION

The following description is provided to enable any person skilled in the art to use the invention and sets forth the best mode contemplated by the inventor for carrying out the invention. Various modifications, however, will remain readily apparent to those skilled in the art, since the principles of the present invention are defined herein specifically to provide a method for sensing changes to a chemical composition based on changes to the plasmon resonance peak generated by a gas sensing material comprised of gold nanoparticles dispersed in an inert matrix.

The disclosure provides a method for sensing changes to a chemical composition by utilizing the changes to the plasmon resonance peak generated by a particular gas sensing material. The gas sensing material is comprised of a plurality of gold nanoparticles dispersed in an inert matrix. The gold nanoparticles have an average nanoparticle diameter of less than about 100 nm, and the inert matrix has a bandgap exceeding 5 eV and an oxygen ion conductivity of less than approximately $10^{-7}$ S/cm at a temperature of 700° C. The method disclosed offers significant advantages over alternative plasmon-based gas sensing materials incorporating active matrix materials such as yttria-stabilized zirconia (YSZ) or $TiO_2$, including enhanced thermal and chemical stability and the ability to tame effective refractive indices in the range required to be compatible with optical waveguide based sensors, and others.

Figure 1:
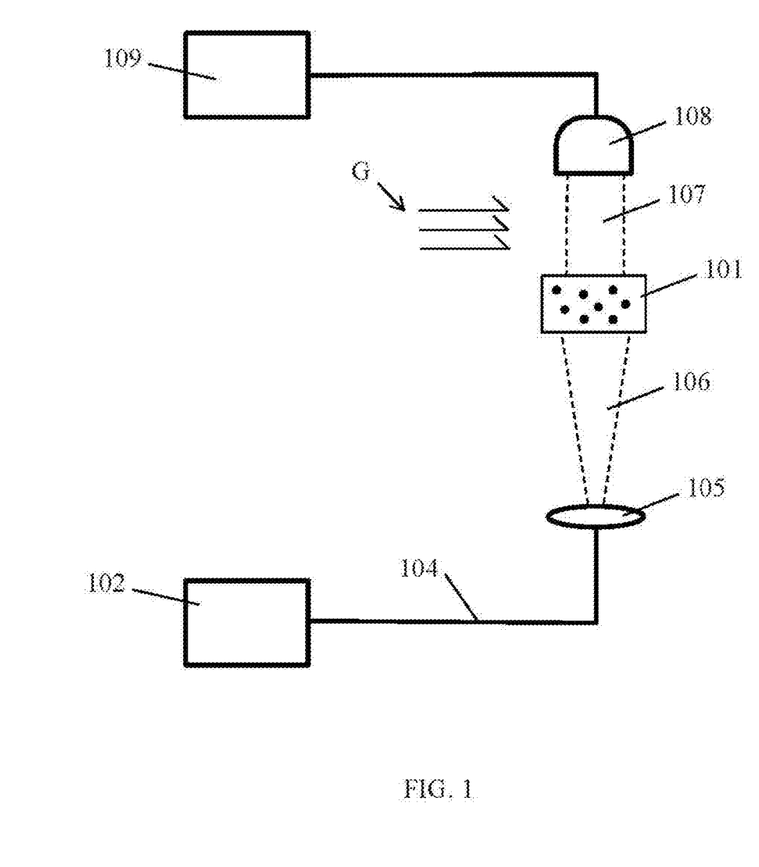
FIG. 1 illustrates a methodology for sensing changes to a chemical composition in a high temperature gas stream using the gas sensing material.

The basic principles of the method are illustrated at FIG. 1. At FIG. 1, light from light source 102 is directed along an optical fiber 104 and focused by lens 105 producing incident light 106 illuminating gas sensing material 101. Generally, incident light 106 is comprised of light having wavelengths in the visible spectrum. Concurrently, exiting light 107 is collected behind the specimen using a probe 108 of spectrophotometer 109. Data generated by spectrophotometer 109 or supporting equipment is processed and the extinction spectrum is displayed. See e.g., Sarid, Dror and Challener, William, *Modern Introduction to Surface Plasmons: Theory, Mathematica Modeling, and Applications*, Cambridge University Press, 2010, among many others. The extinction spectrum indicates the selective photon absorption or scattering of light at certain wavelengths by gas sensing material 101.

Figure 2:
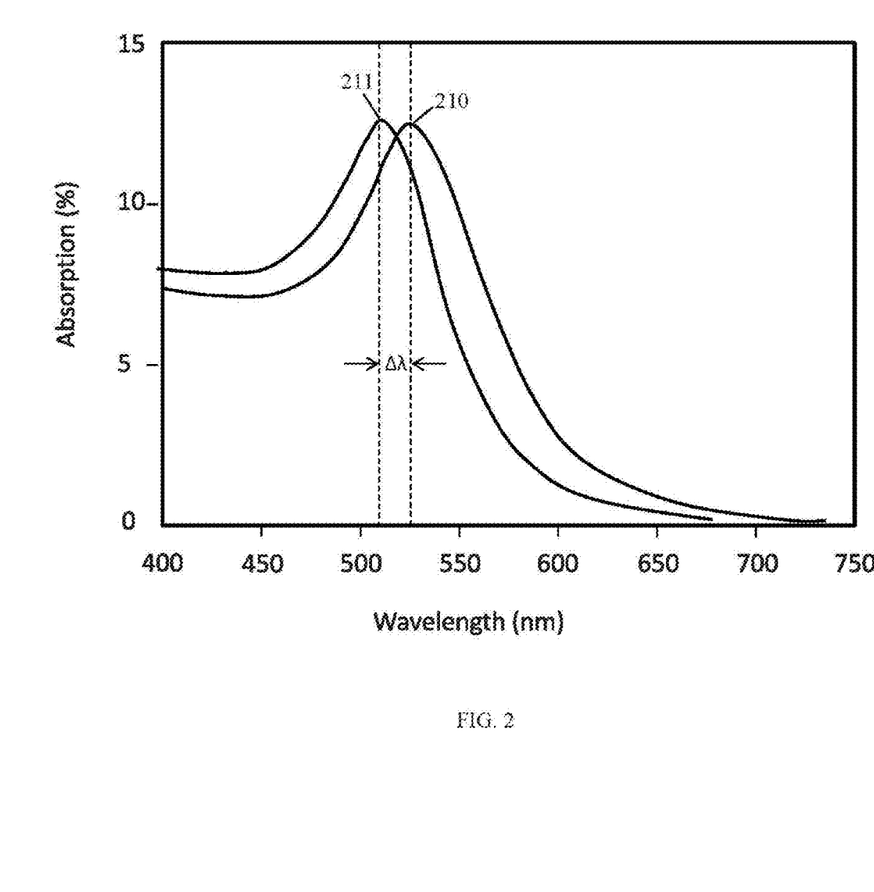
FIG. 2 illustrates an example of a change to the plasmon resonance peak in response to changes to a chemical composition.

Gas sensing material 101 is additionally in contact with a monitored stream G. Monitored stream G is comprised of a chemical composition of gaseous constituents. In an embodiment, monitored stream G is at a temperature greater than 500° C. The gaseous constituents within monitored stream G are periodically comprised of a species of interest, such as CO, $H_2$, and $O_2$, the concentration of which may vary over time. Additionally, and as will be discussed, gas sensing material 101 is comprised of gold nanoparticles dispersed in an inert matrix. It has been found that gas sensing material 101 exhibits a plasmon resonance peak based on the chemical composition of monitored stream G, and that a change in the plasmon resonance peak is indicative of change in the chemical composition. As an example, FIG. 2 illustrates a plasmon resonance peak 210 displaying a plasmon resonance peak position of generally around 525 nm, generated when monitored stream G contacting the gas sensing material is comprised of air with a substantial absence of $H_2$. In contrast, when the chemical composition of monitored stream G is altered, such that monitored stream G is comprised of about 4% $H_2$, remainder $N_2$, the absorption peak blue shifts to plasmon resonance peak 211, with a plasmon resonance peak position occurring at a wavelength of generally around 510 nm. Correspondingly, monitoring the plasmon resonance peak generated by the gas sensing material and detecting a change in the plasmon resonance peak provides a means by which the chemical composition of the monitored stream G may be monitored. With respect FIG. 2, the change in the plasmon resonance peak is detected based on the peak shift Δλ between plasmon resonance peaks 210 and 211. The peak shift Δλ may be monitored directly through broadband wavelength interrogation and appropriate fitting procedures or through indirect measurements by monitoring film transmittance, reflectance, or absorptance at one more selected wavelength(s).

Within this disclosure, "plasmon resonance peak" means the maximum value of absorption which occurs when a spectrum of incident light is compared to a spectrum of exiting light, where the incident light is comprised of light illuminating the gas sensing material, and where the exiting light is comprised of some portion of the incident light transmitted or reflected by the gas sensing material. A "plasmon resonance peak position" means the wavelength at which the plasmon resonance peak occurs. As is understood, absorption spectroscopy based on a comparison of the incident light and the exiting light indicates the light absorption as a function of wavelength that occurs as a result of interaction between the incident light and the gas sensing material, and may serve to identify the plasmon resonance peak of this disclosure. See e.g., Ingle, James D., and Stanley R. Crouch, *Spectrochemical analysis*, Englewood Cliffs, N.J.: Prentice Hall, 1988, among others. Similarly, a "peak shift" means a wavelength shift between a first and second plasmon resonance peak position. For example, peak shift Δλ at FIG. 2. The "plasmon resonance peak breadth" is defined as the full width at half maximum of a fit consisting of a Gaussian, Lorentzian, or some other functional form to a portion of the LSPR absorption peak at wavelengths greater than the plasmon resonance peak position. A "peak broadening" or "peak narrowing" consists of an increase or decrease in the plasmon resonance peak breadth.

Within this disclosure, a "change in the plasmon resonance peak" may mean a peak shift Δλ, where the peak shift Δλ is determined directly in a manner similar to that indicated at FIG. 2, where plasmon resonance peaks are determined and compared to detect a change in the chemical composition of monitored stream G. Alternatively, the change in the plasmon resonance peak may also be recognized by detecting a change in absorption characteristics at any monitored wavelength, or by detecting changes in absorption characteristics at multiple wavelengths over a band of wavelengths. Alternatively, "change in the plasmon resonance peak" may also mean a change in the plasmon resonance peak breadth, a change in the amplitude of the plasmon resonance peak, a change in full width at half maximum (FWHM), or any other techniques utilized to indicate that the absorption characteristics at an individual wavelength or at multiple wavelengths have altered from a monitored plasmon resonance peak.

Figure 3:
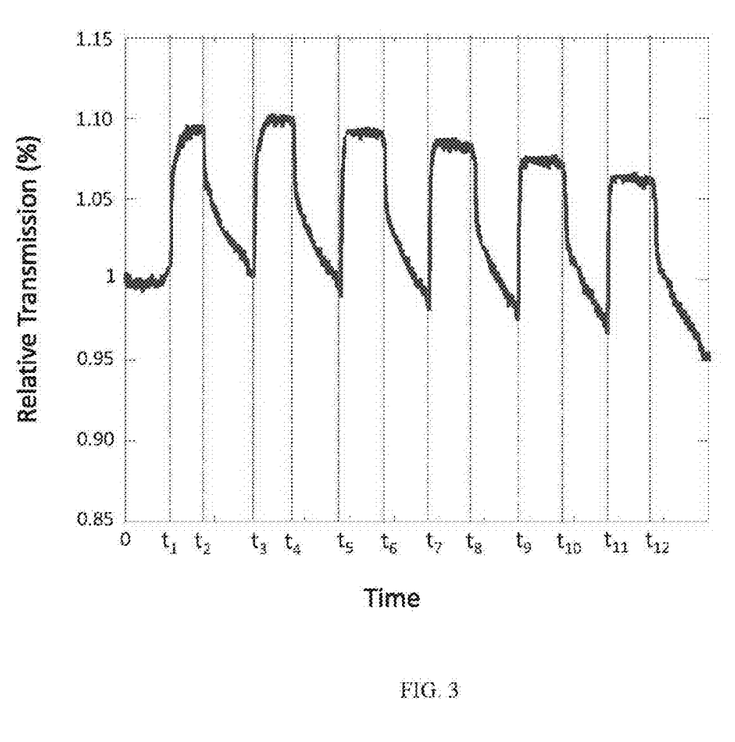
FIG. 3 illustrates the change in transmission characteristics in response to $H_2$ at high temperature at a specific wavelength.

As a further example, where the change in the plasmon resonance peak is detected based on a change in absorption characteristics at a monitored wavelength, FIG. 3 illustrates the response of the gas sensing material in contact with a monitored stream where the change in the chemical composition of the monitored stream is an introduction of $H_2$, and where the gas sensing material is deposited on the core of a fiber-optic waveguide and illuminated by light propagating through the waveguide, as will be discussed. FIG. 3 illustrates a change in relative transmission at a wavelength of 650 nm, where the monitored gas stream is at a temperature of about 850° C. Relative transmission is a transmission proportional to a transmission experienced at a relative transmission of 1.0, so that a relative transmission of 1.1 indicates a 10% increase in transmission over the relative transmission of 1.1, and so on. At FIG. 3, between about times $0$-$t_1$, $t_2$-$t_3$, $t_4$-$t_5$, $t_6$-$t_7$, $t_8$-$t_9$, $t_{10}$-$t_{11}$, and greater than about $t_{12}$, the monitored stream has a background chemical composition of 1% $O_2$ by volume, remainder $N_2$. Between t about times $t_1$-$t_2$, the background chemical composition is altered to include about 0.2% $H_2$, and an increase in the relative transmission of the gas sensing material at the wavelength of 650 nm occurs, as illustrated. Similarly, between about times $t_3$-$t_4$, the background chemical composition is altered to include about 0.4% $H_2$; between about times $t_5$-$t_6$, the background chemical composition is altered to include about 1.0% $H_2$; between about times $t_7$-$t_8$, the background chemical composition is altered to include about 2.0% $H_2$; between about times $t_9$-$t_{10}$, the background chemical composition is altered to include about 3.0% $H_2$; and between about times $t_{11}$-$t_{12}$, the background chemical composition is altered to include about 4.0% $H_2$. As indicated, the relative transmission of the gas sensing material increases at the wavelength of 650 nm for each instance where the chemical composition of the monitored stream is altered through the introduction of $H_2$.

Figure 4:
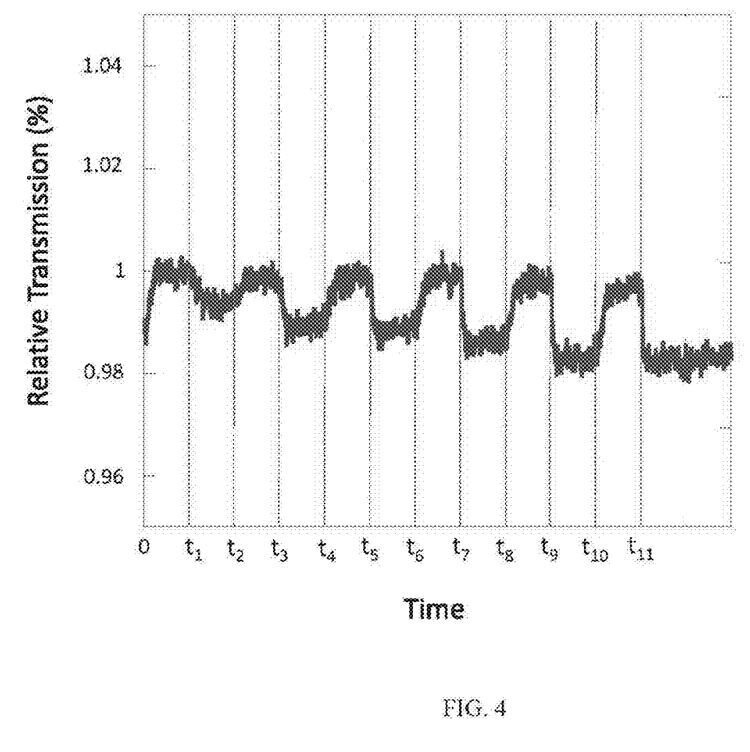
FIG. 4 illustrates the change in transmission characteristics in response to $O_2$ at high temperature at a specific wavelength.

Similarly, FIG. 4 illustrates the response of the gas sensing material when the change in the chemical composition of the monitored stream is an introduction of $O_2$. FIG. 4 illustrates the change in relative transmission at a wavelength of 650 nm and a temperature of about 850° C., and where the gas sensing material is illuminated by an evanescent wave created in a waveguide. At FIG. 4, between about times $0$-$t_1$, $t_2$-$t_3$, $t_4$-$t_5$, $t_6$-$t_7$, $t_8$-$t_9$, and $t_{10}$-$t_{11}$, the monitored stream has a background chemical composition of $N_2$. Between about times $t_1$-$t_2$, the background chemical composition is altered to include about 1% $O_2$ by volume, and a decrease in the relative transmission of the gas sensing material at the wavelength of 650 nm occurs, as illustrated. Similarly, between about times $t_3$-$t_4$, the background chemical composition is altered to include about 3% $O_2$; between about times $t_5$-$t_6$, the background chemical composition is altered to include about 5% $O_2$; between about times $t_7$-$t_8$, the background chemical composition is altered to include about 10% $O_2$; between about times $t_9$-$t_{10}$, the background chemical composition is altered to include about 20% $O_2$; and greater than about time $t_{11}$, the background chemical composition is altered to include about 20% $O_2$. As indicated, the relative transmission of the gas sensing material decreases at the wavelength of 650 nm for each instance where the chemical composition of the monitored stream is altered through the introduction of $O_2$.

Figure 5:
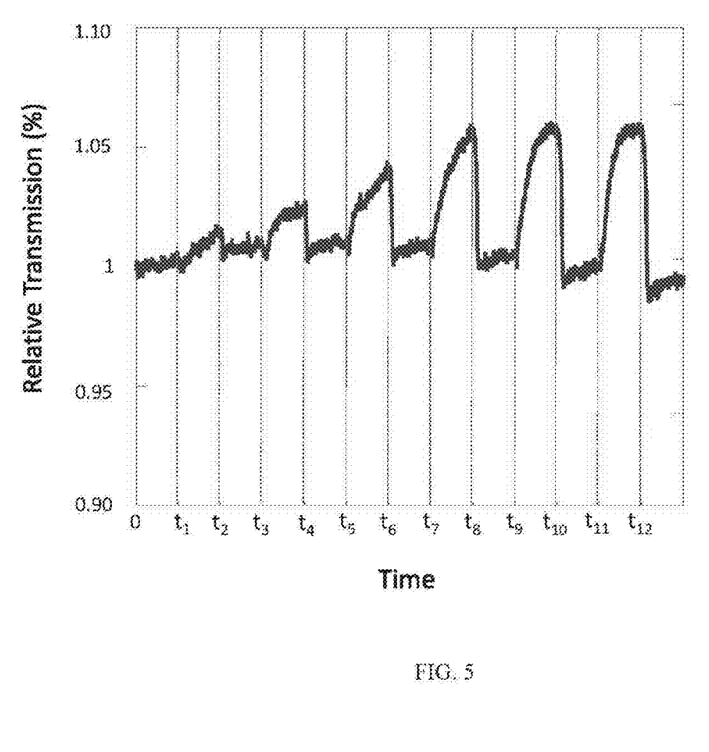
FIG. 5 illustrates the change in transmission characteristics in response to CO at high temperature at a specific wavelength.

In similar fashion, FIG. 5 illustrates the response of the gas sensing material when the change in the chemical composition of the monitored stream is an introduction CO. FIG. 5 illustrates the change in relative transmission at a wavelength of 650 nm and a temperature of about 850° C., and where again the gas sensing material is illuminated by an evanescent wave created in a waveguide. At FIG. 5, between about times $0$-$t_1$, $t_2$-$t_3$, $t_4$-$t_5$, $t_6$-$t_7$, $t_8$-$t_9$, $t_{10}$-$t_{11}$, and greater than about $t_{12}$, the monitored stream has a background chemical composition of 1% $O_2$ by volume, remainder $N_2$. Between about times $t_1$-$t_2$, the background chemical composition is altered to include about 0.5% CO, and an increase in the relative transmission of the gas sensing material at the wavelength of 650 nm occurs, as illustrated. Similarly, between about times $t_3$-$t_4$, the background chemical composition is altered to include about 1 CO; between about times $t_5$-$t_6$, the background chemical composition is altered to include about 2.5% CO; between about times $t_7$-$t_8$, the background chemical composition is altered to include about 5% CO; between about times $t_9$-$t_{10}$, the background chemical composition is altered to include about 7.5% CO; and between about times $t_{11}$-$t_{12}$, the background chemical composition is altered to include about 10% $O_2$. As indicated, the relative transmission of the gas sensing material increases at the wavelength of 650 nm for each instance where the chemical composition of the monitored stream is altered through the introduction of CO.

FIGS. 3-5 serve to illustrate detecting a change in a chemical composition of a monitored stream based on the detection of a change in the plasmon resonance peak, where the change in the plasmon resonance peak is based on a change in absorption characteristics at a monitored wavelength, and when the gas sensing material is in contact with the monitored stream and illuminated with a light source. Examples of gases causing the change in the chemical composition of the monitored stream and which may detected using the gas sensing material as described herein include but are not limited to $H_2$, CO, $O_2$, nitrous oxides (NOx), $N_2$, Ar, $CO_2$, ammonia ($NH_3$), and He. Additional example constituents which may be detected may include sulfur containing species and compounds such as $H_2S$, SOx, and others; trace metals such as Hg, As, Se, Cd, and others; fuel gases such as methane, ethane, and others; and other constituents including but not limited to arsine, phosphine, chlorine, and fluorine.

In an embodiment, the change in the chemical composition of the monitored stream is an increased concentration of a reducing gas, and the increased concentration of the reducing gas is recognized by detecting a peak shift of the plasmon resonance peak position to a shorter wavelength. Here, "reducing gas" means a gaseous constituent considered to be more highly reductive as compared to the inert constituent such as $N_2$, He, or Ar. More specifically, $H_2$, CO, ammonia ($NH_3$), and hydrocarbons (e.g. fuel gases such as methane, ethane) are identified as reducing gases. In another embodiment, the change in the chemical composition of the monitored stream is an increased concentration of an oxidizing gas, and the increased concentration of the oxidizing gas recognized by detecting a peak shift of the plasmon resonance peak position to a longer wavelength. Here "oxidizing gas" means gaseous constituent considered to be more highly oxidative as compared to an inert constituent such as $N_2$, He, or Ar. More specifically $O_2$, $O_3$, NOx, SOx, halogens (e.g. $F_2$, $Cl_2$, $Br_2$, and $I_2$), halogen compounds, sulfuric acids ($H_2SO_4$, $H_2S_2O_8$, and $H_2SO_5$), nitric acid and nitrate compounds are identified as oxidizing gases. The terms "reductive" and "oxidative" within this context refer to a tendency for a chemical species chemisorbed on a Au surface to donate or extract electrons from the underlying Au metal. According to these specifications, chemical constituents such as $H_2$ and CO are excellent examples of reducing gases while $O_2$ is an excellent example of an oxidizing gas.

Gas sensing material 101 is comprised of a plurality of gold nanoparticles dispersed in an inert matrix, where the gold nanoparticles are individually comprised of elemental gold. Preferably, an individual gold nanoparticle is comprised of at least 50 weight percent (wt %) elemental gold, and more preferably, at least 90 wt % elemental gold. Additionally, the plurality of gold nanoparticles has an average nanoparticle diameter of less than about 100 nanometers. The average nanoparticle diameter may be determined using various methods known in the art for the sizing of nanoparticles, for example, scanning electron microscopy (SEM), atomic force microscopy (AFM), and transmission electron microscopy (TEM) methods. Preferably, the average particle size is determined through image analysis by capturing a sample of typically at least 100 nanoparticles, more preferably at least 300 nanoparticles. However, the method by which an average nanoparticle diameter is determined is not limiting within this method. Within this method, it is only necessary that gold nanoparticles are individually comprised of elemental gold, and that the plurality of gold nanoparticles has an average nanoparticle diameter of less than about 100 nanometers. In an embodiment, the average nanoparticle diameter is less than about 50 nanometers. In a further embodiment, the average nanoparticle diameter is less than about 10 nanometers.

It is understood that the nanoparticles of this disclosure are not limited to strictly spherical shapes, and that the plurality of gold nanoparticles may be comprised of shapes such as triangular prisms, disks, shells, wires, rods, and others. When such structures are present, the average particle diameter refers and is equivalent to an equivalent circular diameter (ECD), which connotes the diameter of a circle with area equal to that of the projection of the particle on a plane. See e.g., Xu et al, "Comparison of sizing small particles using different technologies," *Powder Technology* 132 (2003).

Within gas sensing material 101, the gold nanoparticles are dispersed in the inert matrix. As used herein, "dispersed" means that individual gold nanoparticles comprising the plurality of gold nanoparticles in gas sensing material 101 are sufficiently separated such that gas sensing material 101 displays an electrical conductance at least an order of magnitude less than the electrical conductance of bulk gold under an equivalent temperature condition, such that the electrical conductance is less than $1/10^{th}$ of the electrical conductance of the bulk gold. Such a condition can be determined using various methods for the evaluation of proximity to a percolation limit in supported nanoparticle systems. See e.g. Trudeau et al., "Competitive transport and percolation in disordered arrays of molecularly linked Au nanoparticles," *J. Chem. Phys.*, Vol. 117 (2002), among others. Additionally, in an embodiment, an average spacing between individual gold nanoparticles is at least five times greater than the average nanoparticle diameter, where average spacing indicates the average displacement between a gold nanoparticle and a nearest gold nanoparticle neighbor. For a given gold nanoparticle, the nearest gold nanoparticle neighbor may be determined through a variety of statistical methods known in the art, such as fixed radius analysis, minimal spanning trees, Voronoi polygons, k-nearest neighbor algorithms, and other established nearest neighbor methodologies. See e.g., Dussert et al., "Minimal spanning tree: A new approach for studying order and disorder, " *Phys. Rev. B.* 34 (5) (1986), and see Aurenhammer, "Voronoi Diagrams—A Survey of a Fundamental Geometric Data Structure," *ACM Comput. Surv.*, 23(3) (1991), and see Cover et al., "Nearest Neighbor Pattern Classification," *IEEE T. Inform. Theory* 13(1) (1967), among others. The displacement between the given gold nanoparticle and the nearest gold nanoparticle neighbor may be determined using techniques such as scanning electron microscopy, atomic force microscopy, and transmission electron microscopy, and the average spacing may be determined as the average value over some statistically significant population of gold nanoparticles, for example at least 100 gold nanoparticles.

Figure 6:
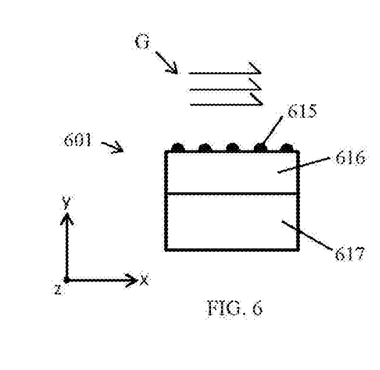
FIG. 6 illustrates an embodiment of the gas sensing material.
Figure 7:
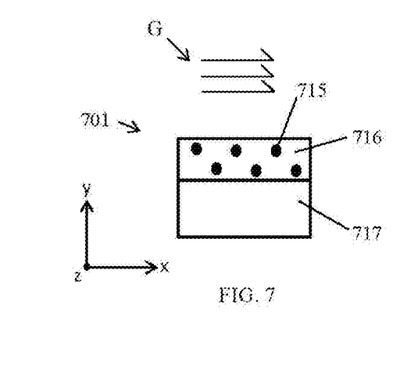
FIG. 7 illustrates an additional embodiment of the gas sensing material.
Figure 8:
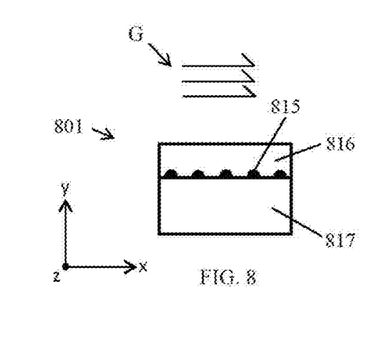
FIG. 8 illustrates an additional embodiment of the gas sensing material.

The gold nanoparticles may be dispersed relatively uniformly or non-uniformly with respect to the inert matrix, provided that the nanoparticles are dispersed within the meaning of the definition discussed above. For example, FIG. 6 illustrates gas sensing material 601 in contact with monitored stream G, where gas sensing material 601 is comprised of a plurality of gold nanoparticles such as gold nanoparticle 615 and an inert matrix 616, and where gas sensing material 601 is further in contact with a substrate 617. At FIG. 6, the plurality of gold nanoparticles are concentrated in a region of inert matrix 616 in spatial proximity to the bulk of monitored stream G, such that the relative concentration of gold nanoparticles decreases or disappears within inert matrix 616 as displacement occurs in a negative direction of the y-axis illustrated. Similarly, FIG. 7 illustrates gas sensing material 701 in contact with monitored stream G, where gas sensing material 701 is comprised of a plurality of gold nanoparticles such as gold nanoparticle 715 and inert matrix 716, and where gas sensing material 701 is further in contact with a substrate 717. In contrast to FIG. 6, at FIG. 7 the plurality of gold nanoparticles are distributed relatively homogeneously through inert matrix 716, such that the relative concentration of gold nanoparticles is substantially similar within inert matrix 716 as displacement occurs in a negative direction of the y-axis illustrated. Additionally, FIG. 8 illustrates gas sensing material 801 in contact with monitored stream G, where gas sensing material 801 is comprised of a plurality of gold nanoparticles such as gold nanoparticle 815 and inert matrix 816, and where gas sensing material 801 is further in contact with a substrate 817, and depicts the plurality of gold nanoparticles concentrated in a region of inert matrix 816 such that the relative concentration of gold nanoparticles increases within inert matrix 816 as displacement occurs in a negative direction of the y-axis illustrated, and decreases or disappears as displacement occurs in a positive direction of the y-axis illustrated. However, arrangements such as those in FIGS. 6, 7, and 8 are exemplary only, and the relative concentrations of gold nanoparticles in varying regions of the inert matrix are not limiting within this disclosure. Within this disclosure, it is only necessary that the gold nanoparticles are sufficiently separated such that the gas sensing material displays an electrical conductance at least an order of magnitude less than the electrical conductance of bulk gold under an equivalent temperature condition, as discussed above.

The inert matrix supporting the plurality of gold nanoparticles is permeable at least to some degree to the incident light at wavelengths corresponding to the plasmon resonance peak positions. For example, when plasmon resonance peak positions are expected to occur within a light wavelength range from about 500 nm to about 650 nm, the inert matrix is permeable at least to some degree to the incident light at wavelengths from about 500 nm to about 650 nm. In an embodiment, the inert matrix is permeable at least to some degree to light at wavelengths over the visible spectrum. Here "visible spectrum" connotes light having wavelengths from about 400 nm to about 750 nm. The optical properties of the inert matrix are such that the inert matrix has a refractive index greater than one.

Additionally, the inert matrix has a bandgap greater than or equal to 5 eV, and has an oxygen ion conductivity less than approximately $10^{-7}$ S/cm at a temperature of 700° C., where the oxygen ion conductivity is either known from compiled sources or determined using techniques known in the art, such as the oxygen permeation method See e.g. Kagomiya et al., "Oxygen permeation and microstructure of intergrowth perovskite Sr—La—Fe—Co based mixed conductive ceramics," *J. Ceram. Soc. Jpn.* 117 (9) (2009); and see Chen et al., "Ionic conductivity of perovskite LaCoO₃ measured by oxygen permeation technique," *J. Appl. Electrochem.* 27 (1997), among others. The inert matrix is generally based upon a stoichiometric dielectric material, such as $SiO_2$, $Si_3N_4$, or $Al_2O_3$. In some cases, the inert matrix may consist of more complex systems such as $MgF_2$-doped $SiO_2$, or mixed $SiO_2$/$Al_2O_3$ to tailor the effective refractive indices for optimized sensing response in optical waveguide based sensing applications. Such an inert matrix as defined within this disclosure has limited free carriers, and can be expected to display negligible change in refractive index in response to reducing species that may occur in a monitored stream even at high temperature conditions of interest. Additionally, the inert matrix acts to mitigate the coarsening of gold nanoparticles which would otherwise occur under the high temperature conditions of this disclosure. The temperatures conditions of this disclosure are well above the Tammann temperature for Gold (about 395° C.) where metal mobility becomes significant. Coarsening of the gold nanoparticles is significantly reduced when dispersed in the inert matrix of this disclosure, as opposed to other common matrix materials such as $TiO_2$. See e.g., Veith et al., "Thermal stability and catalytic activity of gold nanoparticles supported on silica," *J. Catal.* 262 (2009).

Figure 9:
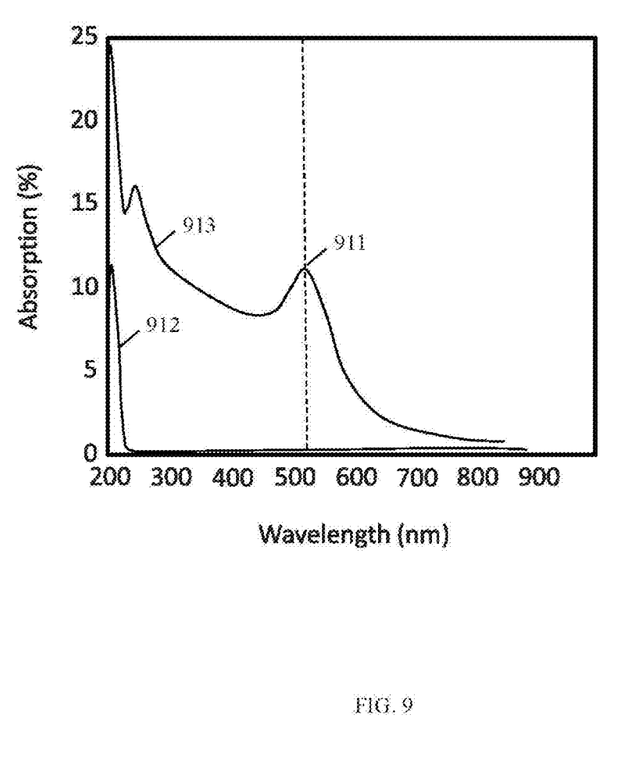
FIG. 9 illustrates a plasmon resonance optical absorption peak for a particular embodiment of the gas sensing material.

FIG. 9. illustrates the plasmon resonance response of a particular embodiment of the gas sensing material and indicates that the plasmon resonance peak observed is dependent on the presence of gold nanoparticles. The particular embodiment illustrated at FIG. 9 is comprised of gold nanoparticles having an average nanoparticle diameter less than about 10 um, dispersed in an $SiO_2$ inert matrix. The quantity Absorption (%) indicates the total amount of incident light on the film absorbed for a given wavelength as indicated based on comparison by absorption spectroscopy between incident light and exiting light following transmission through both the Au/$SiO_2$ material and an $SiO_2$ material without gold nanoparticles present. Response 912 illustrates the absorption of the $SiO_2$ material without dispersed Au nanoparticles, while response 913 illustrates the absorption of the Au/$SiO_2$ material. In contrast to response 912, response 913 indicates a plasmon resonance peak 911 with a plasmon resonance peak position generally around 525 nm, demonstrating the impact of the gold nanoparticles. The gas sensing material of this disclosure is utilized to monitor the chemical composition in a monitored stream based on a modification of plasmon resonance peak 911 in response to changes in the chemical composition of the monitored stream.

Detecting changes to a chemical composition based on changes in the plasmon resonance peak generated by gold nanoparticles dispersed in an inert matrix as described above is a surprising capability. Typically, in gas sensing operations utilizing gold nanoparticles for temperatures at about 500° C. or higher, the gold nanoparticles are embedded in a matrix such as $TiO_2$ or YSZ. At such elevated temperatures in these materials, the bulk defect chemical equilibria are strongly affected by ambient gas conditions, and the materials are oxygen conductors at the temperatures of interest. The sensing mechanism is therefore attributed to the presence of oxygen in the sensing environment and reduction of the matrix, leading to interfacial charge-transfer at the perimeter of the Au nanoparticles which alters the position and shape of the SPR band. For lower temperature applications at about 500° C. and below, gold nanoparticles have been embedded in matrices of even more highly reducible oxides such as NiO, $WO_3$, or CuO. The sensing mechanism is again attributed to reduction of the matrix in the bulk or at the surface, and modifications to the real and imaginary parts of the refractive indices of the oxide may have a relatively more significant impact on altering the position and shape of the SPR band. See e.g., Sirinakis et al., "Development and Characterization of Au-YSZ Surface Plasmon Resonance Based Sensing Materials: High Temperature Detection of CO," *J. Phys. Chem. B* 110 (2006); and see Ando et al., "Optical CO sensitivity of Au—CuO composite film by use of the plasmon absorption change," *Sensors and Actuators B* 96 (2003); and see U.S. Pat. No. 7,864,322 B2 to Carpenter et al. Similarly, in another approach which utilizes gold nanoparticles for $H_2$ detection, atomic H+ may act as a donor to the matrix material, leading to plasmon resonance shifts. See e.g. Joy et al., "Plasmonic Based Kinetic Analysis of Hydrogen Reactions within Au-YSZ Nanocomposites," *J. Phys. Chem. C* 115 (2011). The inert matrix as defined in this disclosure mitigates those modes of operation.

Additionally, gas sensing using gold nanoparticles at elevated temperatures is a surprising capability. Hydrogen uptake by the gold nanoparticles is an example of a possible mechanism for plasmonic sensing with the inert matrix of this disclosure, and activated hydrogen chemisorption occurs as an activated process at temperatures up to at least 250° C. See e.g., Bus et al. However, hydrogen uptake measurements at this lower temperature do not directly extrapolate to the extended temperatures of this disclosure, due to the unknown variance and impact of kinetic and thermodynamic factors on hydrogen adsorption as temperature increases. A useful optical response associated with direct hydrogen chemisorption on Au nanoparticle surfaces at temperatures as high as 900° C. would not be expected or predictable based on low temperature indications of hydrogen uptake.

The gas sensing material utilized in the method of this disclosure may be prepared using means known in the art for the production of gold nanoparticles dispersed in a supporting matrix, including sol-gel wet chemistry based techniques, impregnation techniques, implantation techniques, sputtering techniques, and others. See e.g., De, "Sol-Gel Synthesis of Metal Nanoclusters—Silica Composite Films," *J. Sol-Gel Sci. Techn.* 11 (1998); and see Delannoy et al., "Preparation of supported gold nanoparticles by a modified incipient wetness impregnation method," *J. Phys. Chem. B* 110(45) (2006); and see Veith et al., "Magnetron sputtering of gold nanoparticles onto WO3 and activated carbon," *Catal. Today* 122 (2007); and see Garcia-Serrano et al., "Synthesis and characterization of Au nanoparticles in Al2O3 matrix," *Int. J. Hydrogen Energ.* 28 (2003), among many others. Generally, rigorous calcination schedules will improve the temperature stability of the resulting material under the reducing conditions of this disclosure. A high calcination temperature and long calcination time may ensure that the resulting gas sensing material is properly aged, so that any optical property changes occurring in the material during sensing operations at the higher temperatures of this disclosure can be attributed to changes in the chemical composition of the monitored stream. In an embodiment, treatment temperature is ramped and held at a maximum calcination temperature of at least 800° C. In an additional embodiment, treatment temperature is ramped from about 20° C. to about 950° C. over about 10 hours, held at about 950° C. for about 2 hours, and cooled from about 950° C. to about 20° C. over about 3 hours. However, the specific manner in which the gas sensing material of this disclosure is prepared is not limiting within this disclosure, provided that the gas sensing material is comprised of gold nanoparticles dispersed in an inert matrix as defined herein.

At FIG. 1, the monitored stream G is some portion of a gas stream. In an embodiment, the gas stream and the monitored stream are separated by a barrier layer, such as a dense filter layer to act as a diffusion barrier or a sieve material having an average pore size that is tailored to improve selectivity. Such an arrangement may be helpful when the gas stream is comprised of a molecular constituent which may act to impact the plasmon resonance peak of the gas sensing material, and which may need to be excluded from influencing the sensing operation. For example, a sieve material may be utilized to exclude the molecular constituent from the monitored stream by selecting a sieve material having an average pore size less than the molecular diameter of the molecular constituent to be excluded. Exemplary sieves include aluminosilicate minerals, clays, porous glasses, microporous charcoals, zeolites, active carbons, or synthetic compounds which display a standardized average pore size, such as pore size 3A, pore size 4A, etc. In a similar manner, the dense filter layer can be selected such that the diffusion of a species to be excluded is relatively sluggish. For example, exemplary filters might include films comprised of $SnO_2$, $SiO_2$, Palladium alloys, and others materials known for the selective filtering of hydrogen in an operation where the gas sensing material is utilized to detect changes in an $H_2$ concentration. An appropriately defined barrier layer can also protect the underlying gas sensing layer from the presence of particulates and undesirable corrosive species that may have a deleterious effect on long term stability of the sensing layer. In an embodiment, a first surface of the barrier material is contacted with the high temperature gas stream, and the monitored stream is withdrawn from a second surface of the barrier material.

Figure 10:
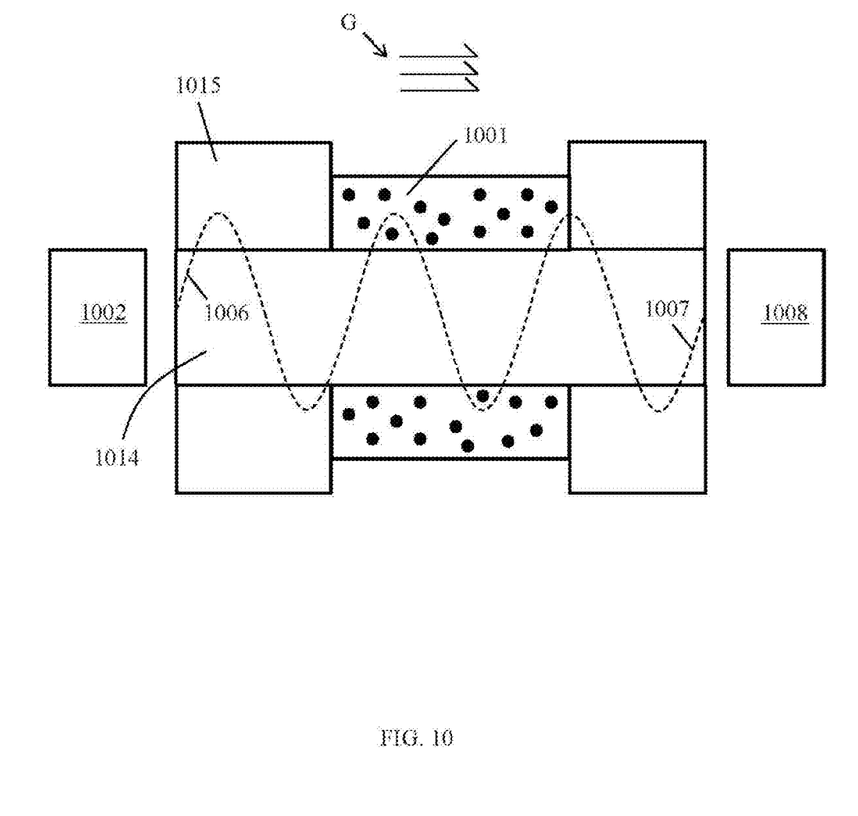
FIG. 10 illustrates a gas sensing material configuration suitable for the detection of changes to a chemical composition using a waveguide sensor.

In another embodiment, the gas sensing material is illuminated by an evanescent wave created in a waveguide, such as a fiber optic cable. This particular embodiment is illustrated at FIG. 10. The waveguide is comprised of a core material 1014 in contact with a cladding material 1015, where core material 1014 has a refractive index greater than cladding material 1015. For example, core material 1014 and cladding material 1015 may be comprised of silica and various additions such as germanium, titanium, phosphorous, boron, fluorine, or other dopants in order to alter the respective refractive indices and meet the necessary criteria. At FIG. 10, light source 1002 emits visible light into core material 1014, generating evanescent wave 1006 penetrating cladding material 1015. As is understood, the optical power and penetration depth of the evanescent wave into cladding 1015 can be described by Beer-Lambert law. See e.g., Dickinson et al., "Convergent, Self-Encoded Bead Sensor Arrays in the design of an Artificial Nose," *Anal. Chem.* 71 (1999), among others. As is similarly understood, the optical power coupled into the evanescent field may be improved by various methods such as bending, optimizing the relative refractive indices of the core and cladding, use of hollow fibers, and other methods. See e.g., Elosua et al., "Volatile Organic Compound Optical Fiber Sensors: A Review," *Sensors* 6 (2006), among others.

At FIG. 10, gas sensing material 1001 having the properties disclosed is placed in contact with core material 1014 such that gas sensing material 1001 is illuminated by evanescent wave 1006 as illustrated. Gas sensing material 1001 is additionally in contact with monitored stream G comprised of gaseous constituents. In an embodiment, monitored stream G has a temperature greater than about 500° C. Exiting light 1007 is collected by probe 1008. Interaction of gas sensing material 1001 with monitored stream G and illumination by evanescent wave 1006 enables detecting a change in the chemical composition of monitored stream G by detecting a change in the plasmon resonance peak, as earlier described.

Thus, provided here is a method for detecting a change in the chemical composition of monitored stream which utilizes changes in the plasmon resonance peak generated by a gas sensing material. The gas sensing material is comprised of a plurality of gold nanoparticles dispersed in a wide bandgap matrix with a low oxygen ion conductivity. The method disclosed offers significant advantage over materials typically utilized for plasmon-based sensing such as yttria-stabilized zirconia (YSZ) or $TiO_2$, including enhanced thermal and chemical stability, relative insensitivity to reducing gases beyond $H_2$, increased stability of nanoparticle diameter, tunability of effective refractive indices for compatibility with optical waveguide based sensors, among others.

It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings

What is claimed is:

1. A method of a detecting a change in a chemical composition of a gas stream comprising:
   generating the gas stream;
   placing a gas sensing material in the gas stream, where the gas sensing material is comprised of,
      an inert matrix, where the inert matrix is stable at the gas stream temperature, and where the inert matrix is optically transparent over a light wavelength range, and where the inert matrix has a bandgap greater than or equal to 5 eV and has an oxygen ion conductivity of less than $10^{-7}$ S/cm at a temperature of 700° C.,
      a plurality of gold nanoparticles dispersed in the inert matrix, where an individual gold nanoparticle in the plurality of gold nanoparticles is comprised of elemental gold, and where the plurality of gold nanoparticles have an average nanoparticle diameter of less than about 100 nanometers;
   contacting the gas sensing material with a monitored stream, where the monitored stream is at least a portion of the gas stream, and illuminating the gas sensing material with a light source emitting incident light;
   collecting exiting light, where the exiting light is light that originates at the light source and is transmitted or reflected by the gas sensing material, and monitoring a plasmon resonance peak based on a comparison of the incident light and the exiting light using absorption spectroscopy; and
   detecting a change in the plasmon resonance peak, thereby detecting the change in the chemical composition, and thereby monitoring the chemical composition of the gas stream.

2. The method of claim 1 where the average nanoparticle diameter is less than about 50 nanometers.

3. The method of claim 2 where the gas stream has a temperature greater than or equal to 500° C., and where the monitored stream has a temperature greater than or equal to 500° C.

4. The method of claim 3 where the change in the chemical composition is an increased concentration of a reducing gas, and further comprised of monitoring a plasmon resonance peak position of the plasmon resonance peak, and where detecting the change in the plasmon resonance peak is comprised of detecting a peak shift of the plasmon resonance peak position to a shorter wavelength.

5. The method of claim 4 where the reducing gas is $H_2$, CO, $NH_3$, a hydrocarbon, and mixtures thereof.

6. The method of claim 5 where the reducing gas is $H_2$, CO, and mixtures thereof.

7. The method of claim 3 where the change in the chemical composition is an increased concentration of an oxidizing gas, and further comprised of monitoring a plasmon resonance peak position of the plasmon resonance peak, and where detecting the change in the plasmon resonance peak is comprised of detecting a peak shift of the plasmon resonance peak position to a longer wavelength.

8. The method of claim 7 where the oxidizing gas is $O_2$, $O_3$, NOx, SOx, a halogen, a halogen compound, a sulfuric acid ($H_2SO_4$, $H_2S_2O_8$, and $H_2SO_5$), a nitric acid, a nitrate, and mixtures thereof.

9. The method of claim 8 where the oxidizing gas is $O_2$, NOx, and mixtures thereof.

10. The method of claim 3 further comprised of monitoring a plasmon resonance peak position of the plasmon resonance peak, where the plasmon resonance peak position is from about 400 nm to about 750 nm.

11. The method of claim 2 where the plurality of nanoparticles is comprised of individual nanoparticles separated by an average nanoparticle spacing, and the average nanoparticle spacing is greater than about 5 times the average nanoparticle diameter.

12. The method of claim 11 where the inert matrix is comprised of $SiO_2$, $Al_2O_3$, $Si_3N_4$, or combinations thereof.

13. The method of claim 1 where the gas stream is comprised of a molecular gas constituent, and further comprising:
   utilizing a barrier layer, where the barrier layer material has a first surface and a second surface, where the first surface and the second surface are separated by at least some portion of the barrier layer; and
   contacting the first surface of the barrier layer and the gas stream, and withdrawing the monitored stream from the second surface of the barrier layer.

14. The method of claim 1 further comprising:
   ascertaining a matrix refractive index, where the matrix refractive index is the refractive index of the inert matrix;
   providing a waveguide comprised of a core material, where the core material has a refractive index greater than the matrix refractive index;
   placing the gas sensing material in contact with the core material; and
   emitting the incident light from the light source into the core material and generating an evanescent wave in the gas sensing material, thereby illuminating the gas sensing material with the light source emitting the incident light.

15. The method of claim 14 where the waveguide is a fiber optic cable having a first end and a second end, and further comprising:
   issuing the incident light from the light source into the core material at the first end of the fiber optic cable, thereby emitting the incident light from the light source into the core material and generating the evanescent wave in the gas sensing material; and
   gathering emitted light from the core material at the second end of the fiber optic cable, thereby collecting the exiting light.

16. The method of claim 15 where the core material is comprised of $SiO_2$, and where the inert matrix is comprised of $SiO_2$.

17. The method of claim 15 where the core material is comprised of $Al_2O_3$, and where the inert matrix is comprised of $SiO_2$ or a mixture of $SiO_2$ and $Al_2O_3$.

18. A method of detecting a change in a chemical composition of a high temperature gas stream comprising:
   generating the high temperature gas stream, where the high temperature gas stream has a temperature greater than about 500° C.;
   placing a gas sensing material in the high temperature gas stream, where the gas sensing material is comprised of, an inert matrix, where the inert matrix is stable at the gas stream temperature, and where the inert matrix is optically transparent over a light wavelength range, and where the inert matrix has a bandgap greater than or equal to 5 eV and has an oxygen ion conductivity of less than $10^{-7}$ S/cm at a temperature of 700° C., a plurality of gold nanoparticles dispersed in the inert matrix, where an individual gold nanoparticle in the plurality of gold nanoparticles is comprised of elemental gold, and where the plurality of gold nanoparticles have an average nanoparticle diameter of less than about 50 nanometers;

contacting the gas sensing material with a monitored stream, where the monitored stream is at least a portion of the high temperature gas stream, and where the monitored stream has a temperature greater than about 500° C., and illuminating the gas sensing material with a light source emitting incident light, where the incident light is comprised of light having a wavelength from about 500 nm to about 650 nm;

collecting exiting light, where the exiting light is light that originates at the light source and is transmitted or reflected by the gas sensing material, and monitoring a plasmon resonance peak based on a comparison of the incident light and the exiting light using absorption spectroscopy; and detecting a change in the plasmon resonance peak, thereby detecting the change in the chemical composition, and thereby monitoring the chemical composition of the high temperature gas stream.

19. The method of claim 18 where the monitored stream is comprised of $H_2$, CO, $O_2$, NOx, or mixtures thereof.

20. The method of claim 18 further comprising:

ascertaining a matrix refractive index, where the matrix refractive index is the refractive index of the inert matrix;

providing a a fiber optic cable having a first end and a second end and comprised of a core material, where the core material has a refractive index greater than the matrix refractive index; placing the gas sensing material in contact with the core material;

issuing the incident light from the light source into the core material at the first end of the fiber optic cable, and generating an evanescent wave in the gas sensing material; and gathering an emitted light from the core material at the second end of the fiber optic cable, thereby collecting the exiting light, and , thereby illuminating the gas sensing material with the light source emitting the incident light.

* * * * *